US00PP19260P2

(12) United States Plant Patent
Korlipara

(10) Patent No.: US PP19,260 P2
(45) Date of Patent: Sep. 23, 2008

(54) ***SCABIOSA* PLANT NAMED 'VIVID VIOLET'**

(50) Latin Name: *Scabiosa*
Varietal Denomination: Vivid Violet

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/904,685

(22) Filed: Sep. 27, 2007

(51) Int. Cl.
*A01H 5/00* (2006.01)

(52) U.S. Cl. ..... Plt./478

(58) Field of Classification Search ..... Plt./478
See application file for complete search history.

(56) References Cited

U.S. PATENT DOCUMENTS

PP12,167 P2 10/2001 Rother

*Primary Examiner*—Annette H Para
*Assistant Examiner*—S. B. McCormick-Ewoldt
(74) *Attorney, Agent, or Firm*—Klarquist, Sparkman, LLP

(57) ABSTRACT

A new and distinct *Scabiosa* plant named 'Vivid Violet' characterized by vivid violet flower color, large flower size, a low, mounding habit, continuous June to October bloom (in Canby, Oreg.), excellent mildew resistance, and excellent vigor.

1 Drawing Sheet

Figure 1:
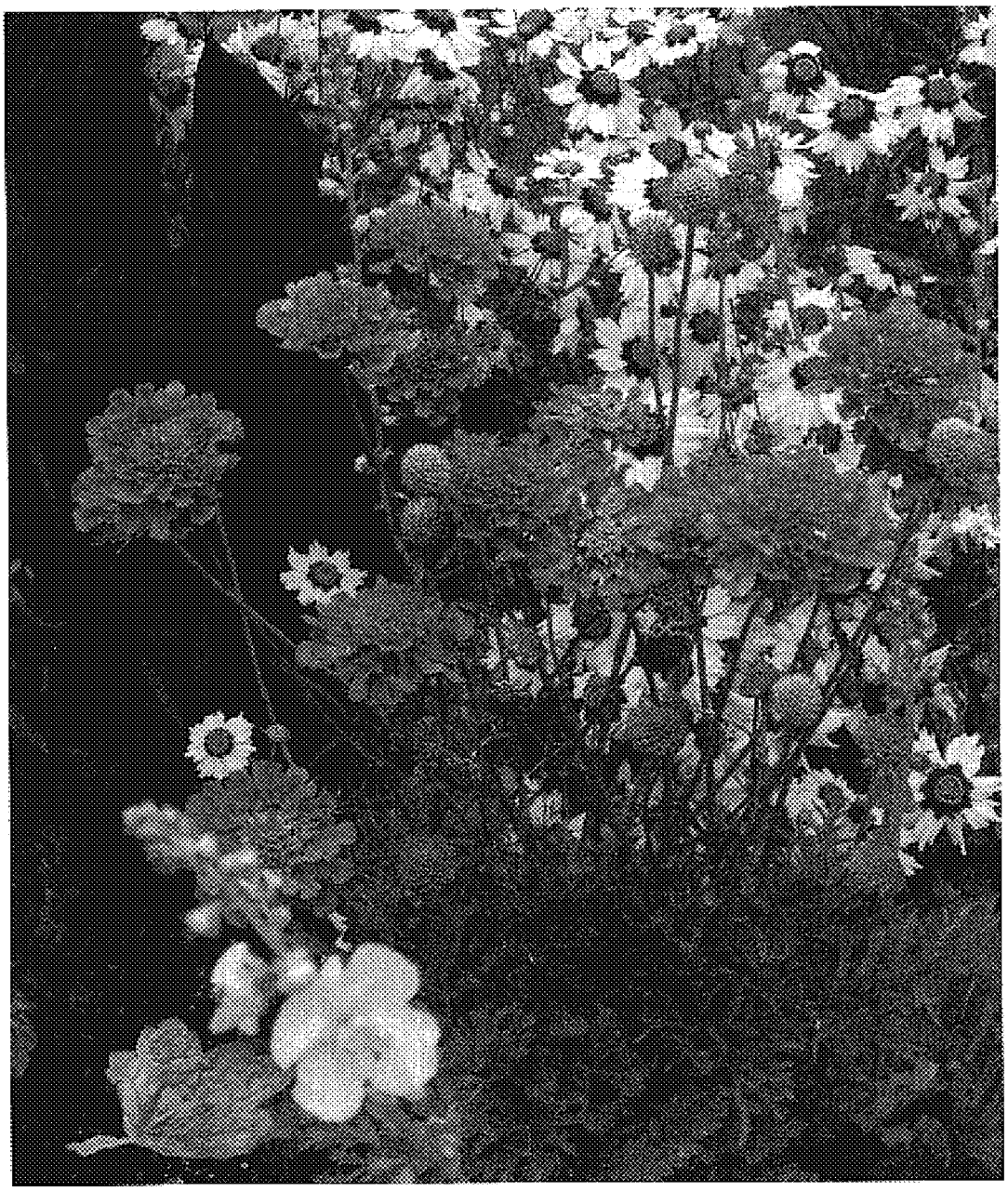

Botanical designation: *Scabiosa* spp.
Variety denomination: 'Vivid Violet'.
Parentage: *S. columbaria* 'Pink Mist'×*S. anthemifolia* 'Giant Blue'.

BACKGROUND OF THE INVENTION

The present invention relates to a new and distinct cultivar of *Scabiosa* plant given the name 'Vivid Violet'. *Scabiosa* is in the family *Dipsacaceae*. This new cultivar originated from a controlled cross between *Scabiosa columbaria* 'Pink Mist' (U.S. Plant Pat. No. 8,957), as the seed parent, and *Scabiosa anthemifolia* 'Giant Blue' (U.S. Plant Pat. No. 12,167), as the pollen parent. The resulting offspring were evaluated and the new invention was selected as superior.

SUMMARY OF THE INVENTION

The following traits have been repeatedly observed and are determined to be the unique characteristics of 'Vivid Violet'. These characteristics in combination distinguish 'Vivid Violet' as a new and distinct cultivar:

1. Vivid violet flower color;
2. Large flower size;
3. Low, mounding habit;
4. Continuous June to October bloom (in Canby, Oreg.);
5. Excellent mildew resistance; and
6. Excellent vigor.

The new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

FIG. 1 shows a 7-month old *Scabiosa* 'Vivid Violet' growing in the ground in the show gardens in full sun in June in Canby, Oreg.

DETAILED PLANT DESCRIPTION

The following is a detailed description of the new *Scabiosa* cultivar based on observations of a nine-month-old specimen grown in the ground in full sun under typical outdoor conditions in the trial fields in September in Canby, Oreg., Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zone 5–9.
- *Size.*—43 cm wide and 20 cm tall to top of the foliage.
- *Form.*—Low mound.
- *Vigor.*—Excellent.

Stem:
- *Type.*—Rosette with branches of side rosettes.
- *Size.*—6 cm long and 3 mm wide, branches of side rosettes grow to 7 cm tall and 1 cm wide.
- *Internode length.*—12 mm long.
- *Surface.*—Pubescent.
- *Color.*—Yellow Green 145C.

Leaf:
- *Type.*—Simple, (basal, rosulate, and cauline).
- *Arrangement.*—Opposite.
- *Surface texture.*—Pubescent on both sides.
- *Venation.*—Pinnate.
- *Petiole base.*—Clasping.

*Color.*—Top side — Green 137A. Bottom — Green 137C. Petiole — Yellow Green 145C.

*Basal leaves.*—Oblanceolate in outline, grow to 17 cm long and 4.5 cm wide, pinnately divided into 7 to 9 main parts and 1 to 9 linear pieces to the petiole base (5 mm wide), divisions obovate, lobed, tips acute, bases attenuate.

*Rosulate leaves.*—Spatulate, irregularly lobed, grow to 13 cm long, blade grows to 5.5 cm long and petiole to 9 cm long and 3 mm wide, tips acute, bases attenuate.

*Cauline leaves.*—Ovate in outline, grow to 4 cm long and 2.5 cm wide, deeply pinnatifid with linear lobes and sometimes secondary lobes, tips acute, bases clasping.

Inflorescence:

*Description.*—Long stalked, hemispherical, terminal heads, with outer florets larger than inner florets, flat topped.

*Mature size.*—Grows to 6 cm wide and 15 mm deep.

*Immature.*—Round, flat topped, 19 mm wide and 10 mm deep, Purple 77A on top surface, Yellow Green 145C on sides.

*Peduncle.*—Grows to 26.5 cm tall and 3 mm wide, pubescent, Yellow Green 146B.

*Involucral bracts.*—10 to 15 in a single row, held horizontally, linear-lanceolate, apex acute, length ranges from 5.0 to 10.0 mm, 1.5 to 3.0 mm in width, base of bract is 145A, portion of bract extended beyond calyces is 137A, pubescent.

*Fragrance.*—None.

*Lastingness of the flower heads.*—Approximately one week in summer and up to two weeks in cool weather.

Flower bud:

*Size.*—10 mm long and 3.5 mm wide.

*Shape.*—Tubular with balled top.

*Surface.*—Pubescent.

*Color.*—Purple 77A to Purple 71A on top and tube Yellow White 158D.

Florets:

*Type.*—Perfect, zygomorphic.

*Number.*—Approximately 37 in number; 11 large outer florets, 7 mid size, and 19 small inner florets.

*Size.*—Largest florets grow to 3 cm long and 1.9 cm wide, tube 1 long and 1 mm wide and small florets are 9 mm long and 3 mm wide.

*Shape.*—Bilabiate with 3 broad flat lobes, terminal lobe the longest, and 2 small lower lobes.

*Lobing.*—5 unequal lobes, pandurate, entire, tip obtuse to notched.

*Surface texture.*—Glabrous on top and pubescent on bottom.

*Color.*—Topside — lobes and throat are bright violet, closest to Violet 86B, Bottom side — Violet 86C on top half of the lobes lightening to Violet 85C on the bottom half of the lobes. Tube — Violet 84A on larger florets and White 155D on small florets.

*Calyx.*—Bristly, of 5 setae, 7 mm long, persistent, Greyed Purple 187A.

*Involucel.*—Persistent at the base of each flower, scarious, White 155D, campanulate, 1.5 mm deep and 1.5 mm wide, margins irregularly serrate.

*Pistil.*—17 cm long, ovary 2 mm long, Yellow Green 145C, pubescent, stigma and style 15 mm long, Violet 86D on top half to White 155D on bottom half.

*Stamen.*—4 in number, anthers 1.5 mm long, White 155D, pollen White 155D, filaments 1 mm long, Violet 86D.

Fruiting inflorescence: persistence and showy.

*Shape.*—Conical.

*Size.*—17 mm long and 15 mm wide.

*Color.*—Clusters of showy seeds with the involucel, White 155A, and setae, Greyed Purple 187A, surrounding the seeds, Yellow Green 144A.

Seed: none viable.

*Fertility.*—Sterile.

Disease and pests: *Scabiosa* are susceptible to mildew and fungal spots. The new variety shows promising resistance to mildew in Canby, Oreg.

COMPARISONS TO SIMILAR *SCABIOSA*

Compared to the pollen parent, *Scabiosa* 'Giant Blue' (U.S. Plant Pat. No. 12,167), this new cultivar has more numerous, smaller, darker violet flowers.

Compared to the seed parent, *Scabiosa columbaria* 'Pink Mist' (U.S. Plant Pat. No. 8,957), the new cultivar has larger, darker violet flowers.

Compared to *Scabiosa columbaria* 'Butterfly Blue' (unpatented), the new cultivar has foliage that is more compact and has flowers that are bigger, brighter and more violet.

I claim:

1. A new and distinct *Scabiosa* plant as herein illustrated and described.

* * * * *

UNITED STATES PATENT AND TRADEMARK OFFICE

CERTIFICATE OF CORRECTION

PATENT NO. : PP 19,260 P2
APPLICATION NO. : 11/904685
DATED : September 23, 2008
INVENTOR(S) : Harini Korlipara It is certified that error appears in the above-identified patent and that said Letters Patent is hereby corrected as shown below:

In the Specification:

Column 1, line 31, “The new” should be --This new--.

Column 2, line 15, “Oreg.,” should be --Oreg.--.

Column 3, line 46, “tube 1 long” should be --tube 1 cm long--.

Signed and Sealed this

Twenty-first Day of April, 2009

John Doll

JOHN DOLL
*Acting Director of the United States Patent and Trademark Office*